US011627904B2

(12) United States Patent
Gogin et al.

(10) Patent No.: US 11,627,904 B2
(45) Date of Patent: Apr. 18, 2023

(54) CARDIAC AND OR RESPIRATORY GATED IMAGE ACQUISITION SYSTEM AND METHOD FOR VIRTUAL ANATOMY ENRICHED REAL TIME 2D IMAGING IN INTERVENTIONAL RADIOFREQUENCY ABLATION OR PACE MAKER REPLACEMENT PROCECURE

(75) Inventors: Nicolas Pierre Bruno Gogin, Paris (FR); Cecile Anne Marie Picard, Sevres (FR); Nicholas Francois Villain, Rueil-Malmaison (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1161 days.

(21) Appl. No.: 13/125,579

(22) PCT Filed: Oct. 19, 2009

(86) PCT No.: PCT/IB2009/054595
§ 371 (c)(1),
(2), (4) Date: Apr. 22, 2011

(87) PCT Pub. No.: WO2010/046838
PCT Pub. Date: Apr. 29, 2010

(65) Prior Publication Data
US 2011/0201915 A1 Aug. 18, 2011

(30) Foreign Application Priority Data
Oct. 23, 2008 (EP) ..................................... 08305719

(51) Int. Cl.
*A61B 5/00* (2006.01)
*A61B 5/352* (2021.01)
(Continued)

(52) U.S. Cl.
CPC .............. *A61B 5/352* (2021.01); *A61B 6/032* (2013.01); *A61B 6/12* (2013.01); *A61B 6/5288* (2013.01);
(Continued)

(58) Field of Classification Search
USPC ................ 600/427, 428, 434, 462, 466–467; 382/128, 154, 164, 171, 174, 190, 285
See application file for complete search history.

(56) References Cited

U.S. PATENT DOCUMENTS 5,643,231 A 7/1997 Lurie et al.
7,203,534 B2 4/2007 Mollus et al.
(Continued)

FOREIGN PATENT DOCUMENTS

CN 101138494 A 3/2008
DE 102007046454 A1 9/2007
(Continued)

OTHER PUBLICATIONS

J. David Burkhardt et al.; "Circulation: Interventional Electrophysiology and Cardiac Resynchronization Therapy: Delivering Electrical Therapies for Heart Failure" Circulation Journal of the American Heart Association; Circulation is published by the American Heart Association. 7272 Greenville Avenue, Dallas; Copyright 2007 American Heart Association. ISSN: 1524-4539; The online version of this article, along with updated information and services, is located on the World Wide Web at: Http://circ.ahajournals.org/cgi/content/115/16/2208.

Primary Examiner — Joel F Brutus

(57) ABSTRACT

The present invention refers to the field of cardiac electrophysiology (EP) and, more specifically, to image-guided radio frequency ablation and pacemaker placement procedures. For those procedures, it is proposed to display the overlaid 2D navigation motions of an interventional tool intraoperatively obtained from the same projection angle for
(Continued)

tracking navigation motions of an interventional tool during an image-guided intervention procedure while being navigated through a patient's bifurcated coronary vessel or cardiac chambers anatomy in order to guide e.g. a cardiovascular catheter to a target structure or lesion in a cardiac vessel segment of the patient's coronary venous tree or to a region of interest within the myocard. In such a way, a dynamically enriched 2D reconstruction of the patient's anatomy is obtained while moving the interventional instrument. By applying a cardiac and/or respiratory gating technique, it can be provided that the 2D live images are acquired during the same phases of the patient's cardiac and/or respiratory cycles. Compared to prior-art solutions which are based on a registration and fusion of image data independently acquired by two distinct imaging modalities, the accuracy of the two-dimensionally reconstructed anatomy is significantly enhanced.

11 Claims, 7 Drawing Sheets

(51) Int. Cl.
| | |
|---|---|
| *A61B 6/12* | (2006.01) |
| *A61B 6/00* | (2006.01) |
| *A61B 6/03* | (2006.01) |
| *A61B 8/08* | (2006.01) |
| *A61B 5/113* | (2006.01) |
| *A61B 90/00* | (2016.01) |

(52) U.S. Cl.
CPC .......... *A61B 8/5276* (2013.01); *A61B 5/1135* (2013.01); *A61B 5/7289* (2013.01); *A61B 6/503* (2013.01); *A61B 6/504* (2013.01); *A61B 6/527* (2013.01); *A61B 6/5235* (2013.01); *A61B 6/5247* (2013.01); *A61B 8/0891* (2013.01); *A61B 90/37* (2016.02); *A61B 2090/364* (2016.02)

(56) References Cited

U.S. PATENT DOCUMENTS

| | | | |
|---|---|---|---|
| 7,729,743 B2 | 6/2010 | Sabczynski et al. | |
| 8,050,739 B2 | 11/2011 | Eck et al. | |
| 8,442,618 B2 | 5/2013 | Strommer et al. | |
| 2001/0016684 A1* | 8/2001 | Shahidi | 600/429 |
| 2002/0140815 A1* | 10/2002 | Herman et al. | 348/180 |
| 2004/0097805 A1* | 5/2004 | Verard et al. | 600/428 |
| 2005/0288578 A1 | 12/2005 | Durlak | |
| 2007/0270689 A1 | 11/2007 | Lothert | |
| 2008/0240536 A1 | 10/2008 | Soubelet et al. | |

FOREIGN PATENT DOCUMENTS

| | | |
|---|---|---|
| JP | 2002058658 A | 2/2002 |
| WO | 2004034329 A2 | 4/2004 |
| WO | 2006066124 A1 | 6/2006 |
| WO | 2006079965 A2 | 9/2006 |

* cited by examiner

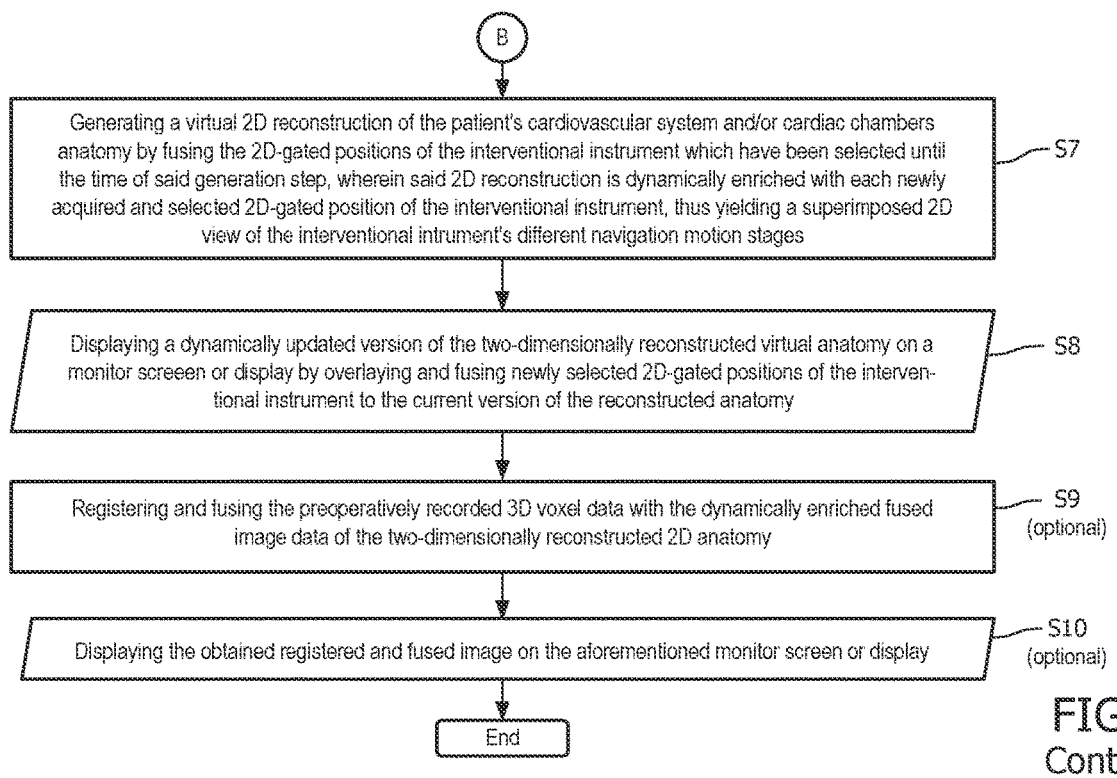
FIG. 1 Continue

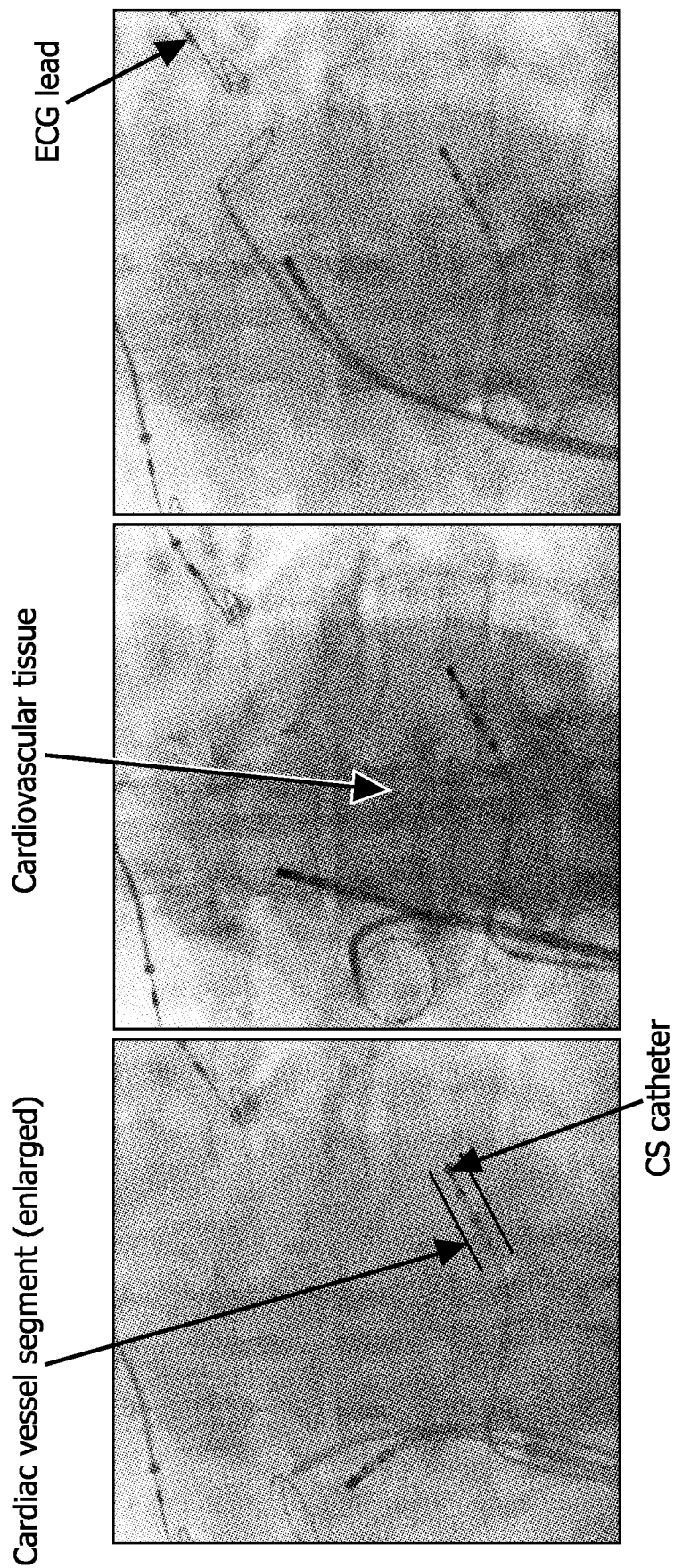

CARDIAC AND OR RESPIRATORY GATED IMAGE ACQUISITION SYSTEM AND METHOD FOR VIRTUAL ANATOMY ENRICHED REAL TIME 2D IMAGING IN INTERVENTIONAL RADIOFREQUENCY ABLATION OR PACE MAKER REPLACEMENT PROCECURE

The present invention refers to the field of cardiac electrophysiology (EP) and, more specifically, to image-guided radiofrequency ablation and pacemaker placement procedures. For those procedures, it is proposed to display the overlaid 2D navigation motions of an interventional tool intraoperatively obtained from the same projection angle during an intervention procedure while being navigated through a patient's bifurcated coronary vessel or cardiac chambers anatomy in order to guide e.g. a cardiovascular catheter to a target structure or lesion in a cardiac vessel segment of the patient's coronary venous tree or to a region of interest within the myocard. In such a way, a dynamically enriched 2D reconstruction of the patient's anatomy is obtained while moving the interventional instrument. By applying a cardiac and/or respiratory gating technique, it can be provided that the 2D live images are acquired during the same phases of the patient's cardiac and/or respiratory cycles. Compared to prior-art solutions which are based on a registration and fusion of image data independently acquired by two distinct imaging modalities, the accuracy of the two-dimensionally reconstructed anatomy is significantly enhanced.

BACKGROUND OF THE INVENTION

Cardiovascular diseases (CVD), such as e.g. atherosclerosis, hypertension and ischemia, are the leading cause of death in most developed countries as they cause permanent damage to the heart and blood vessels that may lead to chronic heart failure, angina, or myocardial infarction (heart attack). For a patient showing symptoms of an electric cardiovascular disease (such as e.g. fibrillation, tachycardia, flutter, etc.) or vessel obstruction, diagnosis and treatment are usually performed via interventional cardiology in a cardiac catheterization laboratory. Cardiac catheterization thereby means insertion of small tubes (catheters) through arteries and/or veins to the myocard. In order to visualize coronary arteries and cardiac chambers with real-time X-ray imaging, a contrast agent is injected through the catheter. The contrast agent has to be opaque to X-rays and provide good image contrast as it flows into the coronary artery system or into the cardiac chambers. This procedure produces an image referred to as an angiogram, which is useful for a physician to navigate in the heart anatomy.

In the last thirty years, minimally invasive X-ray guided interventional cardiology has grown considerably, fueled by demographic, technologic and economic factors. New catheter-based interventional tools (such as e.g. balloon catheters and stents) allow physicians to treat more conditions and more complicated patient cases. As these new minimally invasive, image-guided procedures have positive patient outcomes and are less costly than open-heart procedures, physicians are actively encouraged by governmental and private payers to use these procedures for treating patients.

Nowadays, X-ray based cardiac catheterization systems represent one of the current standards of care and provide imaging modalities for both diagnostic and therapeutic procedures in cardiology. They are applied for generating real-time images of obstructions to blood flow in the coronary arteries. When an obstruction is identified, real-time X-ray imaging is utilized to guide insertion of balloon-tipped catheters to the point of obstruction for treatment by angioplasty (which means by balloon expansion of the restricted flow area in the artery) and stent placement (that is, by expanding a supporting structure to keep the newly enlarged artery open). The goal of therapy for patients with coronary artery disease is to alleviate symptoms of angina and reduce the risk of death or myocardial infarction by employing techniques and devices for reopening the coronary arteries.

A cardiac catheterization system as mentioned above virtually enables all minimally invasive procedures in a catheterization laboratory. Currently developed systems all have the same fundamental architecture and use a point X-ray source that projects an X-ray beam through the patient and onto a large-area detector, the latter being used for converting the generated 2D image to electrical signals for display on a monitor. Thereby, a shadowgram image of the patient is obtained.

Conventionally employed cardiac catheterization systems typically perform two distinct types of real-time X-ray imaging: diagnostic angiography and interventional imaging. Diagnostic angiography is performed with a high radiation exposure in order to produce high-quality images. This diagnostic (cine) mode produces images of injected contrast agent flowing through the coronary arteries to diagnose the initial condition of the coronary arteries, determine the intervention required, and reevaluate the coronary arteries after the intervention. Interventional imaging is performed with a regulated radiation exposure that produces lower-quality images. This interventional (fluoro) mode thereby provides real-time imaging of a patient's anatomy to guide the intervention and is used when inserting devices into the anatomy. The interventional mode is used for approximately 90% of the procedure imaging time.

While cardiovascular diseases primarily affect a patient's blood flow, cardiac electrophysiology (EP), a specific domain of interventional cardiology where physicians use intra-cardiac catheters to locate and cure electrical dysfunctions of the patient's heart rhythm under X-ray fluoroscopy guidance, involves the study of electrical abnormalities of the heart. Congenital problems or diseased tissue in the heart can affect the electrical conduction leading to an irregular heart beat. Aside therefrom, radiofrequency ablation (RFA) for the treatment of atrial fibrillation (AF) is a very challenging EP procedure. Atrial fibrillation is a cardiac arrhythmia associated with significant morbidity and mortality which arises when the two upper chambers of the heart, the left atrium (LA) and the right atrium (RA), do not beat efficiently such that, as a consequence thereof, blood is not pumped completely out of them and may thus pool and clot. If a part of the clot leaves the heart, it may cause a stroke or a pulmonary embolism. Another consequence can be an irregular heart beat transmitted to the ventricles, which will have more impact on the blood circulation. For the treatment of atrial fibrillation, certain areas of tissue may be ablated with radio frequency energy so as to cure the anomalous electrical conduction and to permanently restore the normal heart rhythm. More precisely, the heart tissue is mapped to find the areas of abnormal electrical activity and ablated by cardiac electrophysiology to kill pathological tissue in certain areas. The procedures to locate and ablate the appropriate areas of tissue are extremely lengthy. A patient may spend between three and six hours in the cardiac catheterization laboratory, which may include up to 90 minutes of sheer imaging time. The patient receives significant amounts of X-rays—up to an equivalent of 30,000 chest X-rays—, and the electrophysiologist doing the procedures usually also receives a considerable dose of scattered radiation. Electrophysiology diagnosis and treatment does not require the injection of contrast agent into the coronary arteries to produce detailed images and therefore requires somewhat lower imaging capability. The long procedure times place a high value on radiation exposure reduction.

Another important procedure is the placement of a pacemaker for a cardiac resynchronization therapy (CRT) during which a pacemaker lead has to be placed in a coronary vein. Electrophysiologists need a special training to perfectly know the anatomy and the access pathways to all the sites of interest as well as some practice to select the correct devices and navigate them in a direction towards a target.

The patient's cardiac anatomy can be recorded with conventional 3D imaging devices (such as e.g. CT, MRI, 3DRX or ultrasound examination devices) or by injecting a contrast agent locally just at the beginning of the intervention (left atrium (LA) and ostium of the pulmonary veins (PV) in case of an RFA-based treatment of atrial fibrillation and coronary veins and sinus in case of a CRT), but the physician has to perform mental registration to navigate in the live fluoroscopy images where this information is not visible anymore.

A preoperatively reconstructed 3D map of a cardiac anatomy to be treated can be registered with intraoperatively acquired 2D live images in order to remain visible during the image-guided intervention procedure. On the other hand, such a registration does not take into account a patient's respiratory and cardiac motions, which may lead to the fact that the obtained registration accuracy is not precise enough for some applications. A 3D reconstruction of some cardiac structures can also be obtained by means of magnetically or electrically localized interventional tools, such as used e.g. in the CARTO® RMT electroanatomical mapping system developed by Biosense Webster or in the EnSite NavX™ Navigation & Visualization Technology as proposed by St. Jude Medical.

For AF procedures, knowing the exact positions of the catheters when measuring electrical potentials is key to find the sources that cause fibrillation (ectopic foci, re-entry loop). Even more important is anatomical mapping of the ablation sites in order to perform the desired ablation patterns, such as e.g. pulmonary vein isolation or roof line ablation in the left atrium.

SUMMARY OF THE INVENTION

In view of the above-described facts, it is an object of the present invention to enhance the accuracy of the image-guided interventional procedure by reducing inaccuracies which may arise when registering and fusing images which have been acquired by distinct, independently operated imaging modalities. As most contrast agents are quite expensive and not always well supported by the patients, it is a further object of the present invention to visualize the cardiac vessel structures and/or cardiac chambers anatomy of a patient without needing to inject a contrast agent.

To solve these problems, a first exemplary embodiment of the present invention is directed to an image acquisition method for tracking navigation motions of an interventional instrument while being navigated through a patient's cardiovascular system and/or cardiac chambers anatomy by intraoperatively acquiring and recording a sequence of 2D live images from the same projection angle and object distance, said images showing the interventional instrument during different stages of such a navigation motion. According to the present invention, said method comprises the steps of recording the particular phases of the patient's cardiac and/or respiratory cycles for each track during the acquisition and recording of the 2D fluorograms and selecting a set of those images which correspond to a predefinable specific phase of the patient's cardiac and/or respiratory cycles by means of cardiac and/or respiratory gating. While executing said selection step and further navigating the interventional instrument, a virtual 2D reconstruction of the patient's cardiovascular system and/or cardiac chambers anatomy is generated by fusing the 2D-gated positions of the interventional instrument which have been selected until the time of said generation step, wherein said 2D reconstruction is dynamically enriched with each newly acquired and selected 2D fluorogram, thus yielding a superimposed 2D view of the interventional instrument's different navigation motion stages. Finally, a dynamically updated version of the two-dimensionally reconstructed virtual anatomy is displayed on a monitor screen or display by overlaying and fusing newly selected 2D-gated positions of the interventional instrument to the current version of the reconstructed anatomy. In this way, it can be avoided to perform a preoperative CT, MR or 3DRA scan for acquiring voxel data needed for reconstructing a 3D model of the patient's cardiovascular system and/or cardiac anatomy which, as known from the prior art, is to be coregistered with intraoperatively acquired fluorograms showing the current position of the interventional instrument while being navigated during an image-guided intervention, thus allowing to avoid registration inaccuracies which are to be expected when using distinct imaging modalities for preoperatively acquiring the voxel data of the reconstructed 3D model and the image data of the intraoperatively acquired fluorograms.

According to the invention, the above-described method may preferably be carried out in the scope of an X-ray-guided radiofrequency ablation and pacemaker placement procedure for a cardiac resynchronization therapy during which a pacemaker lead is placed in a coronary vein.

As an additional option, it may be provided that the image acquisition method further comprises the step of performing a CT-, MR- or C-arm based 3DRA image acquisition session for preoperatively acquiring and recording a set of 3D voxel data needed for reconstructing a 3D model of the patient's coronary vessel and/or cardiac chambers anatomy in a region of interest of the patient's cardiac and/or cardiovascular system to be interventionally treated. After that, the preoperatively recorded 3D voxel data can be registered and fused with the dynamically enriched fused data of the two-dimensionally reconstructed 2D anatomy, and the obtained registered and fused anatomy can be displayed on the monitor screen or display.

The above-mentioned step of reconstructing a 3D model of the coronary vessel and/or cardiac chambers anatomy may thereby comprise the steps of calculating an optimal viewing angle with minimum foreshortening and minimum vessel overlap and displaying an optimal view map thereof in a window shown on the monitor screen or display. Furthermore, it may be provided that a 3D segmentation of a target structure or lesion of interest is performed and that image regions which are not included within the segmented contours of said target structure or lesion are faded out.

A second exemplary embodiment of the present invention refers to an image processing system running on a workstation which is coupled to an image acquisition system, wherein said image acquisition system is adapted for executing an image acquisition method for tracking navigation motions of an interventional instrument while being navigated through a patient's cardiovascular system and/or cardiac chambers anatomy by intraoperatively acquiring and recording a sequence of 2D live images from the same projection angle and object distance with said images showing the interventional instrument during different stages of such a navigation motion. According to the present invention, said image processing system is programmed for recording the particular phases of the patient's cardiac and/or respiratory cycles for each track during the acquisition and recording of the 2D fluorograms, selecting a set of those images which correspond to a predefinable specific phase of the patient's cardiac and/or respiratory cycles by means of cardiac and/or respiratory gating and, while executing said selection step and further navigating the interventional instrument, generating a virtual 2D reconstruction of the patient's cardiovascular system and/or cardiac chambers anatomy by fusing the 2D-gated positions of the interventional instrument which have been selected until the time of said generation step, wherein said 2D reconstruction is dynamically enriched with each newly acquired and selected 2D fluorogram, thus yielding a superimposed 2D view of the interventional instrument's different navigation motion stages, and displaying a dynamically updated version of the two-dimensionally reconstructed virtual anatomy on a monitor screen or display by overlaying and fusing newly selected 2D-gated positions of the interventional instrument to the current version of the reconstructed anatomy.

According to a further aspect of this embodiment, said image processing system may be equipped with a 2D/3D registration and fusion tool adapted for registering and fusing a set of 3D voxel data preoperatively acquired and recorded for reconstructing a 3D model of the patient's coronary vessel and/or cardiac chambers anatomy in a region of interest of the patient's cardiac and/or cardiovascular system to be interventionally treated with the dynamically enriched fused image data of the two-dimensionally reconstructed 2D anatomy as well as with a visualization tool for displaying the obtained registered and fused image on the monitor screen or display.

For executing the step of reconstructing the 3D model of the coronary vessel and/or cardiac chambers anatomy, said image processing system may be configured for calculating an optimal viewing angle with minimum foreshortening and minimum vessel overlap and displaying an optimal view map thereof in a window shown on the monitor screen or display. In addition to that, the image processing system may be further adapted for performing a 3D segmentation of a target structure or lesion of interest and fading out image regions which are not included within the segmented contours of said target structure or lesion.

Aside therefrom, a third exemplary embodiment of the present invention is dedicated to a workstation or console. According to the present invention, this workstation or console is programmed with a software which implements an image processing system as described above with reference to said second exemplary embodiment.

Finally, according to a fourth exemplary embodiment of the present invention, a computer software product configured for performing a method as described above with reference to said first exemplary embodiment when running on a workstation or console as described with reference to said third exemplary embodiment is provided.

Compared with other approaches and solutions as known from the prior art, the present invention does not require any registration step with image data from other image data generating modalities, which can be imprecise and may not be motion-compensated. The use of specific localized interventional tools (CARTO, NavX, etc.), which are much more expensive in comparison with the solution as proposed by the present invention, is not necessary any more. Furthermore, the virtual anatomy provided by these known prior-art systems is not directly related to X-ray images, and registration of two modalities can be difficult and inaccurate. By contrast, the virtual anatomy obtained by the proposed approach of the present invention is inherently aligned with fluoroscopy.

BRIEF DESCRIPTION OF THE DRAWINGS

These and other advantageous aspects of the invention will be elucidated by way of example with respect to the embodiments described hereinafter and with respect to the accompanying drawings. Therein.

DETAILED DESCRIPTION OF THE PRESENT INVENTION

In the following, the proposed image acquisition device and method according to the present invention will be explained in more detail with respect to special refinements and referring to the accompanying drawings.

Figure 1:
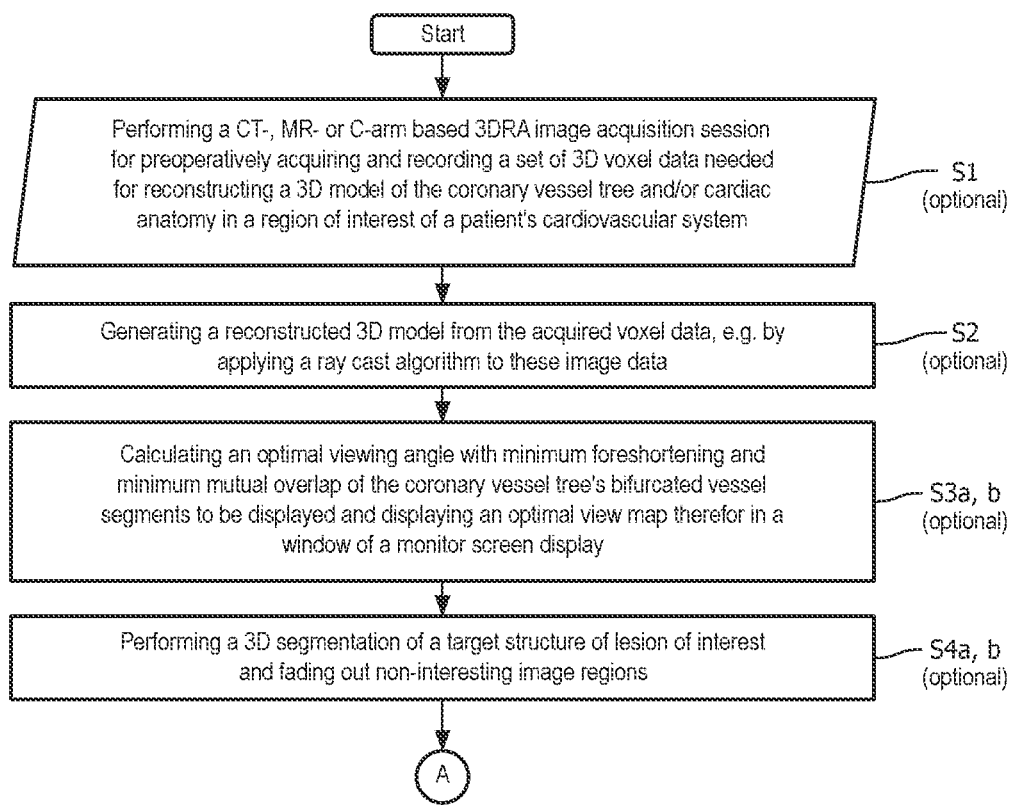
FIG. 1 shows a flowchart which illustrates the proposed image acquisition method according to said first exemplary embodiment of the present invention.
Figure 1:
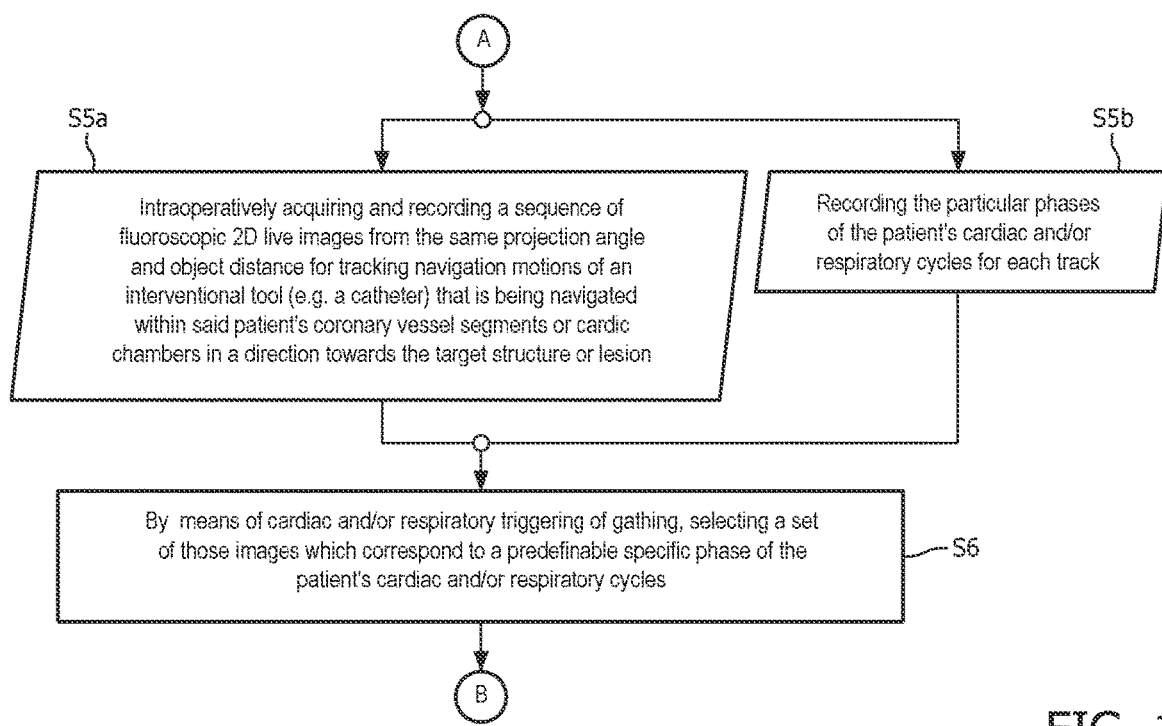

The flowchart depicted in FIG. 1 illustrates the proposed image acquisition method according to the above-described first exemplary embodiment of the present invention. As already mentioned described above, the proposed method begins with the optional step of performing a CT-, MR-, C-arm based 3DRA or any other modality type (ultrasound, scintigraphy, etc.) based image acquisition session for preoperatively acquiring and recording (S1) a set of 3D voxel data needed for reconstructing a 3D model of the coronary vessel tree and/or cardiac anatomy in a region of interest of a patient's cardiovascular system and, after this preoperative image data acquisition step, optionally generating (S2) a three-dimensionally reconstructed model or 3D map of a patient's cardiovascular system in a region of interest to be examined and treated by executing a minimally invasive intervention under fluoroscopic image guidance, such as e.g. a digitally reconstructed radiograph (DRR), from the acquired 3D voxel data. The above-mentioned preoperative image reconstruction step may e.g. be realized by applying a ray cast algorithm to the preoperatively acquired 3D voxel data. After that, it may optionally be provided that an optimal viewing angle with minimum foreshortening and minimum vessel overlap of a coronary vessel tree's bifurcated cardiac vessel segments which are to be displayed is calculated (S3a) such that an optimal view map can be displayed (S3b) on a workstation's monitor screen or display. Further optionally, this optimal view map may then be subjected to a 3D segmentation algorithm (S4) in order to find the contours of a target structure or lesion of interest and fade out non-interesting image regions which are not included within the segmented contours of said target structure or lesion, followed by a filtering and contrast enhancement process which is applied to the segmented image (not shown). After that, a sequence of 2D live images showing the patient's cardiovascular system and/or cardiac anatomy from the same projection angle and object distance is intraoperatively acquired and recorded (S5a) for tracking navigation motions of an interventional tool (e.g. a catheter or guide wire) that is being navigated within said patient's coronary vessel segments or cardiac chambers in a direction towards the target structure or lesion. In parallel to the acquisition of the 2D live images, the particular phases of the patient's cardiac and/or respiratory cycles are being continuously recorded for each track (S5b). As proposed by the present invention, it is provided that a set of those intraoperatively acquired fluorograms which correspond to a predefinable specific phase of the patient's cardiac and/or respiratory cycles is selected (S6) by means of cardiac and/or respiratory triggering or gating. After having generated (S7) a virtual 2D reconstruction of the patient's cardiovascular system and/or cardiac chambers anatomy by fusing the 2D-gated positions of the interventional instrument which have been selected until the time of said generation step, wherein said 2D reconstruction is dynamically enriched with each newly acquired and selected 2D-gated position of the interventional instrument, thus yielding a superimposed 2D view of the interventional instrument's different navigation motion stages, a dynamically updated version of the two-dimensionally reconstructed virtual anatomy is displayed (S8) on a monitor screen or display by overlaying and fusing newly selected 2D-gated positions of the interventional instrument to the current version of the reconstructed anatomy. The preoperatively acquired and recorded 3D voxel data of the segmented target structure or lesion may then optionally be registered and fused (S9) with the dynamically enriched fused image data of the two-dimensionally reconstructed 2D anatomy. The registering procedure thereby yields a best match between said 3D map and the reconstructed 2D anatomy. Finally, the registered and fused image which is obtained in step S9 may be displayed (S10) on the monitor screen or display.

Figure 2:
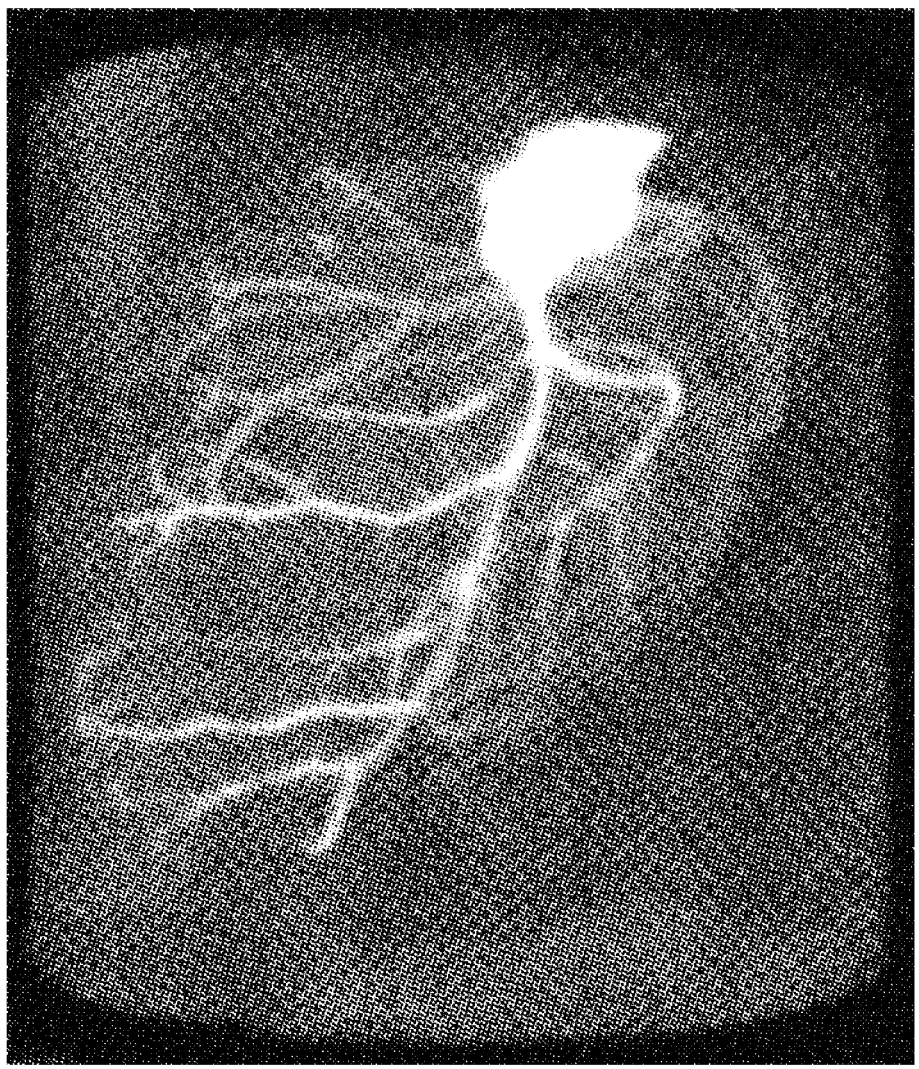
FIG. 2 shows a three-dimensionally reconstructed optimal view map of a patient's left coronary artery tree from an optimal viewing angle yielding minimum foreshortening and minimum vessel overlap.

In FIG. 2, a three-dimensionally reconstructed optimal view map showing a patient's left coronary artery tree from an optimal viewing angle yielding minimum foreshortening and minimum vessel overlap is depicted. The three-dimensional impression can e.g. be obtained by applying a volume rendering technique, a multiplanar reformation procedure or a surface-shaded display algorithm to a set of previously acquired 3D voxel data.

Figure 3A:
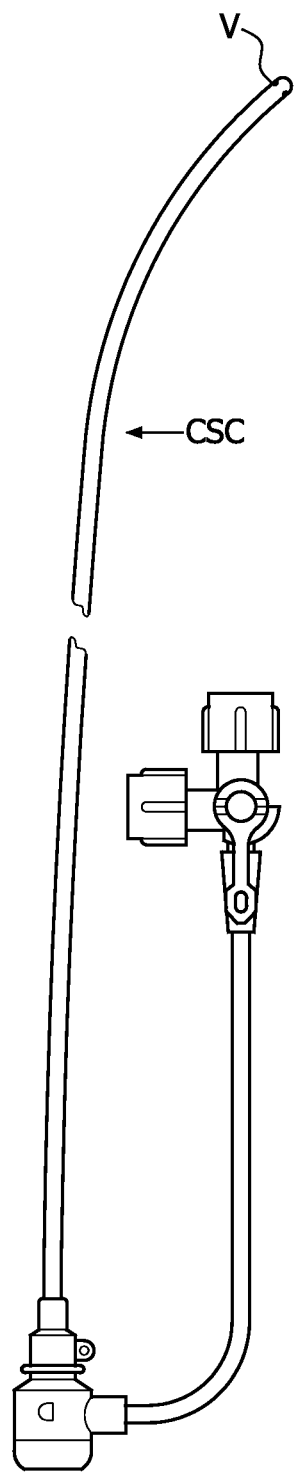
FIG. 3a shows a side perspective view of a coronary sinus catheter as known from the prior art, which is to be navigated through a cardiac vessel segment.
Figure 3B:
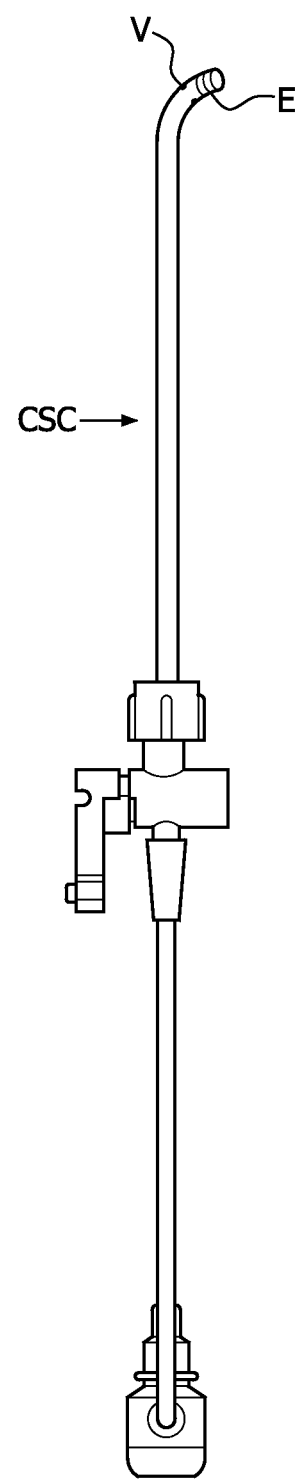
FIG. 3b shows a front view of the coronary sinus catheter depicted in FIG. 3a, FIGS. 4a-c show three subsequently recorded 2D live images of an ablation catheter and a lasso catheter which are being intraoperatively acquired during a cardiac intervention procedure while navigating the cardiovascular catheters in the left atrium and in the pulmonary veins ostia, respectively.

FIGS. 3a and 3b show a side perspective view and a front view of a coronary sinus catheter CSC as known from U.S. Pat. No. 5,643,231 A which is to be navigated through a cardiac vessel segment. Toward the distal end of the catheter, a plurality of electrodes E may be placed, preferably at least two with one of those at the catheter tip. The number of electrodes and their placement on the catheter body thereby depends on the intended usage of the catheter. The ultimate number of electrodes may be as many as ten or more electrodes. If appropriate to the intended use, a lumen may also be incorporated into the catheter for infusion of fluids or withdrawal of blood samples. The diameter of the lumen should be sufficient to accomplish the intended use for the catheter. In the depicted embodiment, one or a plurality of vents V are located near the distal catheter tip with the precise location and number depending on the intended use of the catheter.

In operation, a coronary sinus catheter as depicted in FIGS. 3a and 3b contains electrodes from two to about ten which are connected to an electrophysiology sensing device. The catheter is percutaneously inserted through the internal jugular vein or the subclavian vein and advanced under fluoroscopic control through the superior vena cava to the right atrium. Insertion is also possible using the brachial vein or femoral vein approach via the inferior vena cava. The coronary sinus catheter is then directed across the right atrium until it contacts the ostium of the coronary sinus. The particular structure and curvature of the depicted coronary sinus catheter thereby facilitates the procedure of localizing the ostium of the coronary sinus. Under fluoroscopic guidance the cardiovascular catheter is advanced towards the tricuspid valve with the tip pointed medially. The tip of the coronary sinus catheter is then inserted within the coronary sinus and advanced as far as is required or desired. Continuous and stable recordings of the electrical pathways running near the coronary sinus can then be produced. The curvature of the coronary sinus catheter helps to localize the ostium of the coronary sinus and, in addition, take electrophysiology readings within the coronary sinus. In this manner, the time and X-ray exposure required during the procedure can be reduced.

Aside from being used as a diagnostic electrophysiology catheter, a coronary sinus catheter may also be applied for other medical procedures within the coronary sinus. For example, by modifying the mode of use for the electrodes of the catheter, the types of medical instruments to which the proximal end of the catheter is attached and the electrodes, the catheter can also serve as a means for interventional pacing or permanent pacing of the heart. Pacing with the aid of a coronary sinus catheter will also provide the ability to pace the left atrium. By the administration of a controlled amount of electrical energy to the heart, which is at that time experiencing an arrhythmia, a coronary sinus catheter may also be used for defibrillation purposes or for cardioversion. Furthermore, the catheter may also be utilized for permanent implantable pacing by a few modifications carried out on the catheter.

There are also catheters to perform ablation of the tissues (such as the one presented in FIGS. 4a-c). They often move into the whole left atrium for atrial fibrillation (or into the other cardiac chamber according to the disease to cure).

In FIG. 4a-c, three coronary sinus venographies given in the form of three subsequently recorded 2D live images which are being intraoperatively acquired during a cardiac intervention procedure are shown. Depicted are different stages of an ablation catheter and a lasso catheter while being navigated in the left atrium and the pulmonary veins ostia, respectively, which thus allows to track the navigation motions of these interventional instruments. According to the present invention, those tracks of a cardiovascular catheter and hence those ones of the intraoperatively acquired 2D live images which correspond to a certain cardiac and/or respiratory phase of an electrocardiogram or respirogram, which is/are recorded in parallel during the acquisition of the coronary sinus venographies, are selected by means of cardiac and/or respiratory gating or triggering for being registered and fused with the 3D voxel data of a preoperatively generated optimal view map showing a three-dimensionally reconstructed model of the coronary sinus veins anatomy from an optimal viewing angle with minimum foreshortening and vessel overlap.

Figure 5:
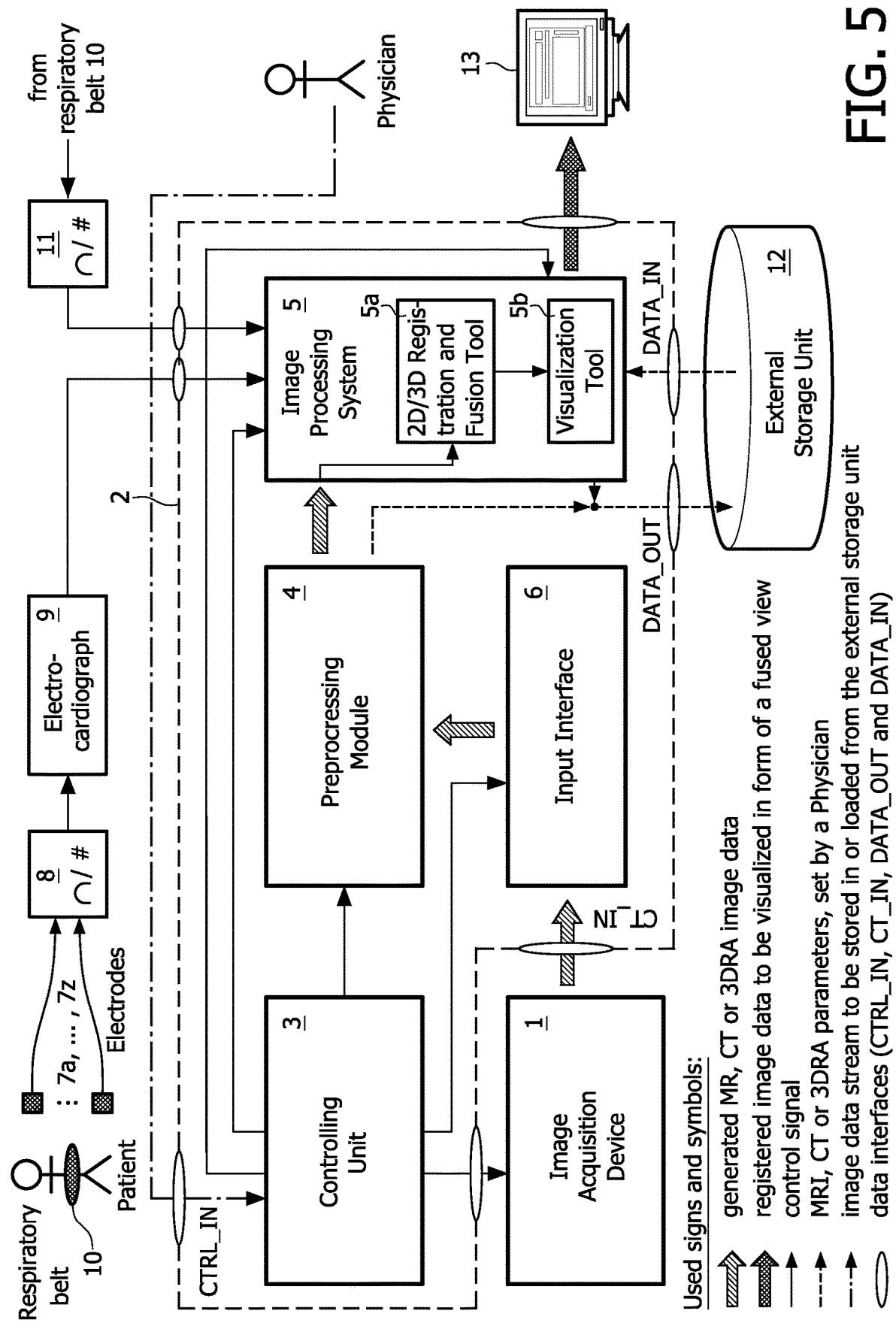
FIG. 5 shows a schematic block diagram of an imaging system according to said third exemplary embodiment of the present invention.

A schematic block diagram of an imaging system 2 according to an exemplary embodiment of the present invention which makes it possible to store, process and visualize acquired image data showing an anatomical structure or a specific region of interest, pathological abnormalities, interventional tools, pacemakers, angioplastic stents or other implants in a blood vessel segment of a patient's vascular system on a monitor screen of a workstation 13 connected to said imaging system 2 is shown in FIG. 5. The image data may e.g. be given in the form of intraoperatively acquired 2D fluoroscopic images, volume-rendered image data or preoperatively recorded 3D voxel data which are generated and provided by an image acquisition device 1, such as e.g. by a magnetic resonance imaging (MRI) system, a computed tomography (CT) system of the rotary-gantry type, a C-arm based 3D rotational angiography (3DRA) device or any other 3D image acquisition system (ultrasound, scintigraphy, etc.). The acquired 2D and reconstructed 3D image data can either be visualized in different windows or in a common window showing a fused view of a digitally reconstructed radiograph that has been generated from the preoperatively recorded 3D voxel data and an intraoperatively acquired 2D image which has been coregistered with said digitally reconstructed radiograph. As shown in FIG. 5, image data generated by said image acquisition device 1 are fed to the imaging system 2 via an input interface 6. Aside from a controlling unit 3 which controls the data exchange with the image acquisition device 1, said imaging system 2 may comprise a preprocessing module 4 which may particularly be equipped with a digital filter for noise reduction and contrast enhancement. An image processing system 5, integrated in said imaging system, may serve for generating volume-rendered 3D views, surface-shaded display (SSD) images, multiplanar reformatted images and/or digitally reconstructed radiographs that are rendered based on the generated 3D voxel data of an anatomical structure or pathological abnormality in a region of interest of a patient's cardiovascular system to be examined and interventionally treated. Said image processing system 5 may be equipped with a 2D/3D registration and fusion tool 5a for determining the parameters of a 2D/3D registration mapping used for registering and fusing the preoperatively generated three-dimensional DRR (or an optimal view map which is generated therefrom) with the dynamically enriched fused image data of the two-dimensionally reconstructed 2D anatomy, said image further showing an interventional instrument or tool while being navigated through a cardiac vessel segment of the patient's depicted vasculature. Optionally, said image processing system 5 may further be equipped with a segmentation tool (not shown) for determining the contours of a target structure or lesion located within said region of interest. A visualization tool 5b, which is integrated in said image processing system 5, may serve for generating and displaying a fused image of the DRR and the 2D image after being submitted to said 2D/3D registration.

FIG. 5 also shows that image data which have been generated by the image acquisition device 1 and supplied to the imaging system 2 via said input interface 6 may temporarily or persistently be stored in an image data archive of an external storage unit 12 via data output interface DATA_OUT. For being visualized, the stored image data can be loaded via a data input interface, in FIG. 5 referred to as "DATA_IN", into a local temporary storage of imaging system 2 (not shown), thereby using a standardized data format (such as e.g. the DICOM format).

For retrospective ECG or respiratory gating, an electrocardiograph 9 and a respiratory belt 10 are connected to an interface terminal of the aforementioned image processing system 5. As an alternative, respiratory motions can be tracked and recorded by other means than a respiratory belt, such as e.g. by tracking of the diaphragm or trachea in fluoroscopy, by tracking of the chest with a camera, etc. Similarly, one could imagine other means to record the cardiac phase (sometimes the heart contour is visible in fluoroscopy, or one could use catheter movements). According to the present invention, the image processing system is adapted to provide a trigger signal for selecting those ones from a sequence of 2D live images intraoperatively acquired for tracking navigation motions of the interventional device while being moved through a patient's bifurcated coronary vessels which correspond to certain cardiac and/or respiratory phases of each track, wherein said trigger signal is derived from the patient's ECG or respirogram that is recorded in parallel during the minimally invasive intervention procedure. For example, those fluorograms are chosen which are acquired at the time when a detected R-wave occurs in the recorded electrocardiogram (which is usually the case during the diastolic phases).

According to an alternative of the above-described embodiment, two independently operated image acquisition systems are used. A first image acquisition system is employed to generate real-time 2D fluoroscopy images of an anatomical region of interest during an interventional procedure. Optionally, due to the fact that this modality does not allow clear visualization of complex soft tissue anatomy such as e.g. the myo card, a second image acquisition system may be applied which generates reconstructed 3D maps of a patient's cardiovascular anatomy from a set of 3D voxel data preoperatively acquired by means of CT, 3DRA, MRI or other technology. During the interventional procedure, an interventional instrument, such as e.g. a cardiovascular catheter, is navigated in a region of interest through the particular vessel segments of a coronary venous tree's bifurcated cardiac veins (in case of a pacemaker lead placement) or in a direction towards the left atrium (in case of an AF procedure), whereas other procedures may require to navigate this one or another type of interventional instrument towards other regions of interest.

The invention thereby provides that the tracks of the interventional instrument are segmented out and recorded over time. In parallel, a system is used for triggering respiration and cardiac motion. This can be done by dedicated devices, such as e.g. by ECG devices for cardiac triggering, a respiratory belt for respiration triggering or by means of a coronary sinus (CS) catheter for both. Alternatives thereto have been mentioned above. Thereby, corresponding phase information is combined with the recorded tracks of the applied interventional instrument.

The proposed system displays in real-time a superposition of such tracks that correspond to the current respiratory and cardiac phase. This additional information is used to image and dynamically update a patient's cardiac anatomy in 2D, thus yielding an anatomy-enriched impression of this navigation motion which helps a clinician to visualize an anatomy region of interest while carrying out a cardiac intervention procedure. The interventional instrument may thereby be moved in order to explore the coronary sinus veins anatomy and in order to enrich the dynamically reconstructed virtual 2D anatomy. After that, a preoperatively reconstructed 3D map or an endoscopic image may optionally be registered and fused with the dynamically updated image data of the two-dimensionally reconstructed 2D anatomy showing the navigation motions of the interventional instrument, and it may further be provided that said virtual anatomy is colored to differentiate it from the anatomical structures and the interventional instrument depicted in the intraoperatively acquired 2D live images.

APPLICATIONS OF THE PRESENT INVENTION

The present invention can advantageously be applied in the scope of minimally invasive image-guided interventions where it is beneficial to reduce the X-radiation dose to which a patient to be interventionally treated is exposed during a radiographic image acquisition session, such as e.g. in the scope of X-ray-guided radio-frequency ablation or pacemaker placement procedures. The proposed system and method are especially intended for being applied in a medical workstation or console, particularly in those dedicated to electrophysiology procedures, such as e.g. Philips' EP Navigator.

While the present invention has been illustrated and described in detail in the drawings and in the foregoing description, such illustration and description are to be considered illustrative or exemplary and not restrictive, which means that the invention is not limited to the disclosed embodiments. Other variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as e.g. an optical storage medium or a solid-state medium supplied together with or as part of other hardware, but may also be distributed in other forms, such as e.g. via the Internet or other wired or wireless telecommunication systems. Furthermore, any reference signs in the claims should not be construed as limiting the scope of the present invention.

The invention claimed is:

1. An image acquisition method for tracking navigation motions of an interventional instrument while being navigated through a cardiovascular system or cardiac chambers anatomy of a patient, the image acquisition method comprising:
    intraoperatively acquiring and recording 2D live images from a same projection angle and object distance, the 2D live images showing the interventional instrument during different stages of the navigation motions;
    recording phases of a cardiac or respiratory cycle of the patient during the acquiring and recording of the 2D live images;
    selecting a set of the 2D live images which correspond to a specific phase of the cardiac or respiratory cycle of the patient using cardiac or respiratory gating; and
    while selecting the set of the 2D live images and further navigating the interventional instrument,
    generating a 2D reconstruction of the cardiovascular system or cardiac chambers anatomy of the patient by fusing an overlay of the set of the 2D live images showing the interventional instrument at different navigation motion stages, wherein the 2D reconstruction is dynamically enriched by overlaying and fusing each newly acquired and selected 2D live image, and
    displaying the 2D reconstruction of the cardiovascular system or cardiac chambers anatomy on a monitor screen or display for tracking the navigation motions of the interventional instrument while being navigated through the cardiovascular system or cardiac chambers anatomy of the patient.

2. The image acquisition method according to claim 1, carried out during a radiofrequency ablation and pacemaker placement procedure for a cardiac resynchronization therapy during which a pacemaker lead is placed in a coronary vein.

3. The image acquisition method according to claim 1, further comprising:
    performing a CT-, MR-, or C-arm based 3D image acquisition session for preoperatively acquiring and recording a set of 3D voxel data needed for reconstructing a 3D model of the cardiovascular system or cardiac chambers anatomy of the patient in a region of interest of the cardiovascular system of or cardiac chambers anatomy of the patient to be interventionally treated;
    registering and fusing the set of 3D voxel data with the 2D reconstruction; and
    displaying the 2D reconstruction registered and fused with the 3D voxel data on the monitor screen or display.

4. The image acquisition method according to claim 3, wherein reconstructing the 3D model of the cardiovascular system or cardiac chambers anatomy of the patient comprises calculating an optimal viewing angle with minimum foreshortening and minimum vessel overlap, and displaying an optimal view map thereof in a window shown on the monitor screen or display.

5. The image acquisition method according to claim 3, wherein reconstructing the 3D model of the cardiovascular system or cardiac chambers anatomy comprises performing a 3D segmentation of a target structure or lesion of interest and fading out image regions which are not included within segmented contours of the target structure or lesion.

6. A workstation or console, comprising at least one processor and at least one memory, and a program of instruction encoded on the at least one memory that, when executed by the at least one processor, performs the method according to claim 1.

7. A system comprising:
    an image acquisition device that intraoperatively acquires and records 2D live images from a same projection angle and object distance, wherein the 2D live images show an interventional instrument during different stages of a navigation motion, respectively;
    means for recording phases of cardiac cycles of a patient and/or means for recording respiratory cycles of the patient during the acquiring and recording of the 2D live images;
    an image processing system that selects 2D live images, from the 2D live images, that correspond to a specific phase of the cardiac or respiratory cycles of the patient using cardiac or respiratory gating, the selected 2D live images showing the interventional instrument at the different navigation motion stages, and that generates a 2D reconstruction of a cardiovascular system or cardiac chambers anatomy of the patient by fusing an overlay of the 2D live images showing the interventional instrument at the different navigation motion stages, while selecting the 2D live images and while the interventional instrument is further navigated, wherein the 2D reconstruction is dynamically enriched by overlaying and fusing each newly acquired and selected 2D image; and a display that displays the 2D reconstruction of the cardiovascular system or cardiac chamber anatomy of the patient for tracking the navigation motion stages of the interventional instrument while being navigated through the cardiovascular system or cardiac chambers anatomy of the patient.

8. The system according to claim 7,
wherein the image processing system comprises:
a 2D/3D registration and fusion tool that registers and fuses a set of 3D voxel data, preoperatively acquired and recorded for reconstructing a 3D model of the cardiovascular system or cardiac chambers anatomy of the patient, with the 2D reconstruction; and
a visualization tool that displays the 3D voxel data fused with the 2D reconstruction on the display.

9. The system according to claim 8, wherein the image processing system calculates an optimal viewing angle with minimum foreshortening and minimum vessel overlap, for displaying an optimal view map thereof in a window shown on the display.

10. The system according to claim 9, wherein the image processing system performs a 3D segmentation of a target structure or lesion of interest and fades out image regions which are not included within segmented contours of the target structure or lesion.

11. A computer program product for implementing image processing, the computer program product comprising instructions which, when executed by a computer, cause the computer to carry out a method, comprising:
intraoperatively acquiring and recording 2D live images from a same projection angle and object distance, the 2D live images showing an interventional instrument during different stages of a navigation motion of the interventional instrument through a cardiovascular system or cardiac chambers anatomy of a patient;
recording phases of cardiac or respiratory cycles of the patient during the acquiring and recording of the 2D live images,
selecting a set of the 2D live images which correspond to a specific phase of the cardiac or respiratory cycles of the patient using cardiac or respiratory gating, the selected set of 2D live images showing the interventional instrument at different stages of the navigation motion; and
while selecting the set of the 2D live images, and further navigating the interventional instrument,
generating a 2D reconstruction of the cardiovascular system or cardiac chambers anatomy of the patient by fusing an overlay of the selected set of 2D images showing the interventional instrument at the different stages of the navigation motion, wherein the 2D reconstruction is dynamically enriched by overlaying and fusing newly acquired 2D live images of the interventional instrument and selected sets of the newly acquired 2D live images, and
causing display of the 2D reconstruction of the cardiovascular system or the cardiac chambers anatomy of the patient on a monitor screen or display enabling tracking of the navigation motion of the interventional instrument through the cardiovascular system or cardiac chambers anatomy of the patient.

* * * * *